United States Patent [19]

Steinemann et al.

[11] 4,040,129
[45] Aug. 9, 1977

[54] SURGICAL IMPLANT AND ALLOY FOR USE IN MAKING AN IMPLANT

[75] Inventors: Samuel G. Steinemann, St-Sulpice; Stephan M. Perren, Davos, both of Switzerland

[73] Assignee: Institut Dr. Ing. Reinhard Straumann AG, Switzerland

[21] Appl. No.: 552,216

[22] Filed: Feb. 24, 1975

Related U.S. Application Data

[63] Continuation-in-part of Ser. No. 382,194, July 24, 1973, abandoned, which is a continuation-in-part of Ser. No. 162,269, July 13, 1971, abandoned.

[30] Foreign Application Priority Data

July 15, 1970 Switzerland ............... 10721/70

[51] Int. Cl.$^2$ ............... A61F 1/24; A61B 17/18; C22C 14/00; C22C 11/00
[52] U.S. Cl. ............... 3/1.9; 3/1.91; 128/92 B; 128/92 BA; 128/92 BC; 128/92 C; 128/92 D; 32/10 A; 75/175.5; 75/177; 148/11.5 F; 148/32.5
[58] Field of Search ............... 75/175.5, 177, 174, 75/134 F, 134 N, 138, 176; 128/83, 92 R, 92 C, 92 B, 92 BA, 92 BC, 92 D; 3/1.9, 1.913, 1.91; 32/10 A; 148/32, 32.5, 11.5 F

[56] References Cited

U.S. PATENT DOCUMENTS

| | | | |
|---|---|---|---|
| 2,892,706 | 6/1959 | Jaffee et al. | 75/175.5 |
| 2,948,607 | 8/1960 | Wagener | 75/175.5 |
| 3,370,946 | 2/1968 | Bertea et al. | 75/175.5 |
| 3,777,346 | 12/1973 | Steinemann | 75/177 |

OTHER PUBLICATIONS

Hoar, T., et al.; *Corrosion-Resistant Alloys... for Surgical Implants*, in *Proc. Roy. Soc.* (294) London 1966, pp. 486-510.

Mears, D.; *Electron-Probe Microanalysis ... Implant Areas*, in *Journ. Bone & Joint Surg.*, 48b, Aug. 1966, pp. 567-576.

Ferguson, et al.; *Metal Implants in Living Tissues*, in *Journ. Bone & Joint Surg.*, 42a, Jan. 1960 pp. 77-90.

*Primary Examiner*—Walter R. Satterfield
*Attorney, Agent, or Firm*—McGlew and Tuttle

[57] ABSTRACT

Implant for bone surgery and for dental therapeutics, comprising an alloy containing defined critical amounts of titanium and/or zirconium, and other selected elements including niobium, tantalum, chromium, molybdenum and aluminum. Dissolved gases may also be included. The alloy is free from copper, cobalt, nickel, vanadium and tin, apart from the usual impurities.

18 Claims, 6 Drawing Figures

SURGICAL IMPLANT AND ALLOY FOR USE IN MAKING AN IMPLANT

This application is a continuation-in-part of application Ser. No. 382,194 filed July 24, 1973 and now abandoned which, in turn, is a continuation-in-part of application Ser. No. 162,269 filed July 13, 1971 and now abandoned.

BACKGROUND OF THE INVENTION

1. Field of the Invention

This invention relates in general to the construction of implants and, in particular, to a new and useful implant alloy and to the use of an improved alloy for body implants.

2. Description of the Prior Art

Implants for surgery are made from stainless steel (standards: USA ASTM F55, ASTM F 56; GB Brit. Standard 3531-1962), cobalt alloys under the trade names Vitallium and others (standards: USA ASTM F54; British Standard 3531-1962), titanium (standards: USA ASTM F67-66; British Standard 3531-1962/1967) and a Ti 6Al 4V-alloy (standard for clinical tests in USA: ASTM 1968). The second material is a cast alloy; of such cast materials it is known that porosities may occur and without particular techniques, such alloy has a very coarse grain structure. However, for surgical implants, these are undesired properties, since coarse grain reduces the strength of the alloy and controlling freedom from pores in the alloy is expensive.

All the metals show sufficient tissue compatibility.

The following Table 1 gives information about the mechanical properties of the named materials for implants.

TABLE 1

| Material | tensile strength Kg/mm² | elongation % | fatigue strength kg/mm² | elasticity modulus kg/mm² |
|---|---|---|---|---|
| Stainless steel annealed | 60 | 40 | 30 | 19000 |
| Stainless steel cold formed | 90-100 | 15 | 40 | 19000 |
| Technically pure Titanium | 55 | 40 | 28 | 11000 |
| Vitallium, cast and annealed | 55 | 10 | 28 | 20000 |

The view that implants of stronger dimensioning are necessary for operative fracture treatment is only valid as regards strength, which is necessary to prevent fatigue-conditioned breakage of the implant. The strong dimensioning, however, also makes implants mechanically stiff. Implants which are too rigid, however, do not permit functional loading of the bone bridged by the implant, and there results dangerous weakening of the bone substance or decalcification and further fractures. The ratio of tensile strength to elasticity modulus for stainless steel is 100/20000 and for titanium is 55/11000, which is therefore about as much. The ratio is low, and the strength of a biomechanically favorably dimensioned implant, i.e., of adapted rigidity, is insufficient to eliminate complications because of implant breakage. The tensile strength should preferably amount to at least 100 kg/mm², and the fatigue strength should amount to about 60 kg/mm².

A further requirement for implant materials is full tissue compatability. Ferguson, et al. (Journal of Bone and Joint Surgery 41A, 737, 1959; id. 42A, 77, 1960; 44A 323, 1962; Journal of Biomedical Materials Research 1, 135, 1967) in experiments on the rabbit after implantation over some months, have measured the concentration of the metal lying in the tissue, and they have characterized reactions of this tissue. The results are shown in the following Table 2.

TABLE 2

| Material | metal enrichment in the tissue | includes toxic elements | reaction of the tissue |
|---|---|---|---|
| Stainless steel | 1,7 ppm | Ni | connective tissue up to ca. 100μm |
| Vitallium | 1,6 ppm | Co | connective tissue up to ca. 100μm |
| Titanium | 2,6 ppm | none | connective tissue under ca. 15μm |

The strong membrane of connective tissue around stainless steel and cobalt alloys is a rejection reaction of the body. On the other hand, the toxicity examinations of Hulliger, et al. (Zeitschrift fur die gesamte experimentelle Medizin 144, 145, 1967) show growth inhibition on connective tissue cultures in the presence of metals and their chlorides for Cu, Co, Ni, Sb, Sn, Zn, etc. These are the toxic reactions which lead to encapsulation and inflammations and therefore restrict the tissue vitality.

Electrochemical methods alone are suitable for measuring the extraordinarily small corrosion of resistant metals in the body. For the "in vitro"-experiment, electrolytes of similar composition as body liquid are needed. "In vivo"-experiments are used because only then the Redox process operates correctly, and also direct effects of the adjacent, displaced tissue are determinable. In such experiments, the test metal with an insulated contact wire and a flexible tubing, used as salt bridge arriving at the surface of the test metal and connected to a reference electrode is introduced in the experimental animal (rabbit) and for the measurement, the salt bridge and the conductor to the metal are connected to the measurement apparatus, while the auxiliary electrode is put onto the skin. The so-called polarization resistance is measured, which may be converted into the corrosion current and corrosion rate. After 3 to 8 weeks, during which the corrosion is repeatedly determined, the animal is sacrificed and tissue lying on the implanted metal is examined histologically.

Each metal, even Pt, corrodes in the body liquid and results in corrosion products (hydroxides, oxides in different oxidation states, chlorides, sulfides, etc.). These corrosion products arrive through mechanical transport (phagocytes, etc.) and chemical transport (solution, dissociation and reprecipitation) into the tissues and the circulatory system. The corrosion is always stronger than the ability of the body to transport away all corrosion products; tissue reactions are the result (connective tissue is formed, necrosis, inflammations). These reactions are on the basis of the histological examination classified in three groups:

1. "Sterile abscess", in which the tissue lying on the metal is necrotic and round cells exist, and the connective tissue is pervaded only within a moderate distance with blood vessels and capillaries;
2. Encapsulation of the foreign body through more or less thick connective tissue, but lacking inflammationary reaction; and
3. Filling up reaction through loose connective tissue, without encapsulation and vascularization up to the metal, therefore full vitality.

In the following Table 3, several results of corrosion experiments in vivo in rabbits and hisological results are put together. Further, they contain element data. The metals with an electrical lead and salt-bridge to reference electrode are implanted and measured periodically by polarization resistance technique.

TABLE 3

| Material | corrosion current A/cm$^2$ | corrosion rate g/cm$^2$ | tissue reaction |
|---|---|---|---|
| Nickel | $1 \cdot 10^{-7}$ | 4 | sterile abscess (animal after 2-3 weeks dead) |
| Iron | $1 \cdot 10^{-6}$ | 20 | encapsulation without inflammation |
| Aluminum | $4 \cdot 10^{-7}$ | 2 | |
| Stainless steel | $1 \cdot 10^{-9}$ | 0,1 | |
| Titanium | $7 \cdot 10^{-10}$ | 0,007 | |
| Zirconium | $7 \cdot 10^{-10}$ | 0,012 | loose, thin connective tissue, vascularized; full vitality |
| Platinum | $1 \cdot 10^{-8}$ | 0,3 | |
| Tantalum | $5 \cdot 10^{-9}$ | 0,12 | |
| Niobium | $2 \cdot 10^{-9}$ | 0,03 | |

Results concerning tissue reaction are obtained from rabbit tests at the same time as the corrosion measurement (histology after sacrificing the animal) and from separate tests of implanted metals in rabbits and rats. D. C. Mears, "Journal of Bone and Joint Surgery", Vol. 48B, p. 567 (1966) suggests titanium-niobium, titanium-tantalum alloys (page 575, line 8) ". . . be discarded in favor of more inert materials - such as cobalt, chromium alloys, pre titanium . . .". The sense of the word "inert" is here "chemically inert" and, in relation to low corrosion rate and has to be distinguished from the notion "non-toxic". In fact, Mears mixes in the same phrase also alloys with cobalt which is explicitly a toxic element.

In group 1 in particular, the metals Cu, Co, Ni, V and Sn are included, and in group 2, fall stainless steels, vitallium, Ag, Au, Al, Fe, Cr, and Mo. It is apparent that for groups 1 and 2, a strong tissue reaction is not unconditionally interrelated with strong corrosion. Al and Fe corrode strongly like Ni, but have a harmless reaction. Group 3 comprises the five last-mentioned elements of Table 3.

SUMMARY OF THE INVENTION

According to the present invention, there is provided an alloy for use in making a surgical implant, comprising from 3% to 30% of a material consisting of one or more of the elements niobium, tantalum, chromium, molybdenum and aluminum, and a metallic remainder consisting essentially of one or more of the elements titanium and zirconium, the sum of the contents of chromium, molybdenum and aluminum being at most 20% by weight of the alloy, the zirconium content being at most 75% by weight of the alloy, and the alloy being free from copper, cobalt, nickel, vanadium and tin, apart from usual impurities.

A homogeneous alloy corrodes essentially with all its components. The concentration sums of various elements are important.

Up to a certain concentration, even elements of higher toxicity than Ti, Zr, Ta, Nb, Pt may be added, in which case, the extraordinarily high corrosion resistance of the Ti and Zr based alloys remains. In this regard, for example, aluminum is notable. So Al is in many cases contained in Ti alloys. The element is slightly toxic, but the high solubility of the hydroxides makes it harmless in a corrosion resistant alloy. For V, another alloy element, this is true only restrictedly, and the known α/β-alloy with 6 weight % Al, 4 weight % V, remainder Ti contains the toxic element V.

Dissolved gases (containing e.g., $O_2$, $N_2$, C, $H_2$) may be accommodated as interstitial atoms. Thee elements increase strength.

These alloys combine corrosion resistance, compatability and high strength (up to 140 kg/mm$^2$) for uses in surgery and dental therapeutics; they are the ideal metal for implants, and the small density of titanium-rich alloys brings advantages.

The surgical implants of the present invention may be cast, hot worked or forged and eventually cold worked. The alloy compositions of the invention are called "wrought alloys" herein and are meant to include the alloy composition which is obtained "as cast". By "hot working" is understood "forging".

GENERAL DESCRIPTION OF SPECIFIC EMBODIMENTS

Figure 1:
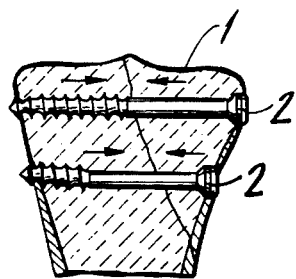
FIG. 1 is a sectional view showing a tooth structure with internal fixation devices therein.

The special alloys which are used according to the invention for making surgical and dental implants must withstand corrosion within the living system and avoid any chemical interaction in vivo which would result in a toxic reaction harmful to the living subject. Certainly such harmful reaction is to be avoided. Tests of the wrought alloy implants of the invention have shown that such implants are safe and effective for use on living mammalian subjects.

The following discussion of implants illustrates the invention. In bone surgery and dental surgery and orthopedices, these are the following types of implants:

a. for internal fixation (also called open reduction of fractures) and for orthopedics -
 bone screws — bone plates of various sizes (section small, heavy and of different length spoken of as number of holes) — bone plates of particular shape (angulated plates, small plates made of sheet for small bones or hand surgery, jaw, etc.) — intramedullary nails, pins or wires for cartilage, etc.
b. prosthetic devices
hip prosthesis — knee prosthesis — skull plates -etc.
c. for dental surgery and dentistry — screws fixed in bone as stud, plates with stud inserted in bone, screws going through root of tooth and holding in bone, etc.

Referring to the drawings in particular, the invention embodied therein in the various figures show representative forms of implants constructed in accordance with the invention.

Figure 3:
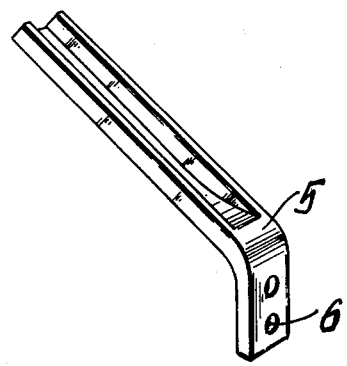
FIG. 3 is a top view of another plate member for internal fixation.
Figure 2:
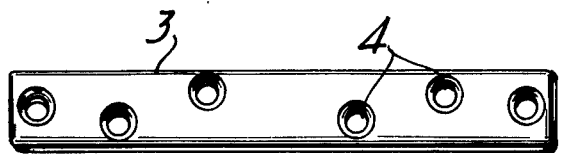
FIG. 2 is a perspective view of a plate member for internal fixation.

As shown in FIG. 1, implants such as bone screws 2 are used to secure a fractured tooth 1. In FIGS. 2 and 3, implants or bone plates, such as 5 and 3 have holes 4 and 6 for securing the plates in the living subject. At such holes and elsewhere under living conditions, corrosion or toxic reactions can occur on such plates. FIG. 2 shows a broad plate 3, and FIGS. 3 shows an implant comprising a femoral neck plate 5.

Figure 4:
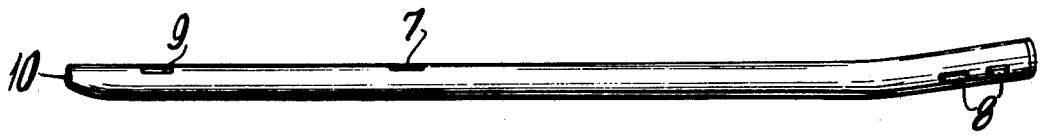
FIGS. 4, 5 and 6 are further perspective views of other internal fixation devices for prosthetic or orthopedic uses.

FIG. 4 shows an implant comprising a Tibial nail having openings 7, 8, 9 and 10. These openings are of varying shapes and can be the site of corrosion or toxic reation in vivo.

Figure 5:
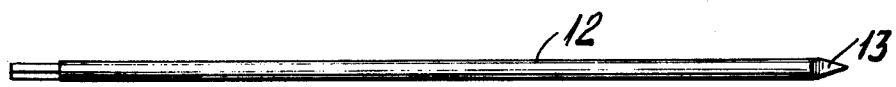
Figure 6:

FIG. 5 illustrates an implant comprising a Steinmann pin 12 with Trocar point 13, while FIG. 6 shows a Schanz screw 14 with screw threads 15.

All of these illustrative devices in FIGS. 1-6 are examples of internal fixation devices which are made of the critical alloy defined and made according to the present invention. It is extremely important to select the right combination of selected elements as described herein for making the surgical and dental implants.

The invention requires that the alloy should be made from certain chosen elements. By itself, this is new. It is in fact quite surprising to find the defined combination to be so safe and effective. There are some 50 metallic elements which can be alloyed in theory to titanium and zirconium. According to the present invention, only 7 of them are effective and safe and recommended for use. Practical titanium alloys comprise alloying elements such as Zr, Al, V, Nb, Ta, Mo, Mn, Cu, Sn, W, Cr, Co, Ni, Fe, etc. According ot the present invention, V, Cu, Co, Ni, Sn are explicitly to be suppressed and excluded as alloying elements and Mn and others are not selected. This result comes from in vivo and in vitro studies which show that all elements in the metal have in principle in action on tissue whatever the corrosion rate (all metals corrode). Let us look at the situation: a) In principle 50 elements can be alloyed to Ti or Zr and this makes 50 systems of binary alloys or even 1.50.49 = 2500 ternary alloy systems; according to our discovery and invention only 7 elements should be used, thus 1.7 binary and 1.7.6 ternary alloy systems. Out of 50 possible are elected 7 binary and out of 2500 possible ternary are elected 42 ternary systems.

The present application explains that it is not sufficient that the metal has a low corrosion rate but that above it all constituents must by themselves be non-toxic. Let us compare such requirements with the use of titanium in other fields:

TABLE 4

|  | good strength | corrosion behavior | effects with corrosion products |
|---|---|---|---|
| construction material (for example aircraft) | Yes | rate not so important, resistant to stress corrosion | not important |
| chemical industry nuclear engineering | less important | rate low, resistant to stress corrosion | not or occasionally important, no elements which produce catalytic reactions or could become radioactive |
| Implants | Yes | very low rate, resistant to stress corrosion | very important in that no toxic element should be present |

Clearly, the conditions for implants are very special. We list the best known titanium alloys practically used today:

Ti 6 Al 4 V
Ti 13 V 11 Cr 3 Al
Ti 2 Cu
Ti 11 Sn 2.5 Al 5Zr 1 Mo
Ti 4 Al 4 Mn
Ti 8 Al 1 Mo 1 V

All of the foregoing contain at least one element proscribed in this application. The critical choice of alloying elements is clear according to our discovery. Tests have been carried out to establish this criticality:

in vitro test of actions of metals on fibroblast cultures
in vitro test of action of metal chlorides upon growth of organ cultures of embryonic chicken femora
in vivo tests by implanted metals in forms of plates and small cylinders.

The following alloys as examples, may be used:

EXAMPLE 1

6 weight % Al
3 weight % Nb
remainder Ti.

This is an α-β-phase alloy, which in the annealed state possesses a tensile strength of 95 kg/mm$^2$ and in fully heat treated condition (solution anneal, quench and precipitation hardening) a tensile strength of about 120 kg/mm$^2$. The elongations are 15% and 10% respectively, and the fatigue strength amounts to up to 70 kg/mm$^2$.

EXAMPLE 2

30 weight % Nb
remainder Zr.

This alloy has, after annealing at 950° C, cold forming of ca. 20% and heat treatment at ca. 700° C over 10 hours, a tensile strength of over 120 kg/mm$^2$.

EXAMPLE 3

8 -9 weight % Nb
11 weight % Cr
3 weight % Al remainder Ti.

This is a β-alloy, which in the annealed condition has a tensile strength of about 90 kg/mm² and in fully heat treated condition reaches strengths up to 140 kg/mm².

EXAMPLE 4

The alloy with
5 weight % Ta
remainder Ti
has, when annealed, a strength of 75 kg/mm², and after ca. 30% cold forming of 90 — 100 kg/mm².

EXAMPLE 5

The alloy with
30 weight % Ta
remainder Ti
is an α-β-phase alloy with a strength of about 80 kg/mm² in the annealed condition.

EXAMPLE 6

48 weight % Zr
4 weight % Mo
remainder Ti.

This is an α-β-phase alloy which, when annealed, has a strength up to 90 kg/mm² and good ductility for working.

EXAMPLE 7

30 weight % Nb
2 weight % Zr
remainder Ti.

The alloy has after annealing at 900° C for 1 hour, quenching and subsequent heat treatment at 450° C for 10 hours to 650° C for 1 hour, a strength of at least 90 kg/mm².

The production of implants may be done on annealed material and a heat treatment to raise strength can follow, and even perhaps high temperature anneal, quenching and hardening heattreatment such as referred to in Examples 1, 2, 3 and 7. The annealing and quenching are then advantageously carried out before the shaping production (by cutting, milling, electrochemical machining) steps, and the heat-treatment after the latter. For strength augmentation, also cold forming is suitable (Example 4).

These alloys may be worked in a similar way to titanium.

Furthermore, for implants surface treatments may also be employed, such as oxidation, nitridation, carbonitridation, etc.

What is claimed is:

1. Implant for bone, joint or dental surgery consisting essentially of a worked and heat-treated alloy composition having full tissue compatibility and a tensile strength of not less than about 100 kg/mm² and fatigue strength of at least about 40 kg/mm², said alloy composition consisting essentially of:
   i. a first component constituting about 3% to about 30% by weight of said alloy composition, said first component consisting essentially of not less than one member selected from the group consisting of niobium, tantalum, chromium, molybdenum, aluminum; and the balance
   ii. a second component of said alloy composition consisting essentially of not less than one member selected from the group consisting of titanium and zirconium;

wherein the sum of the weights of chromium, molybdenum, and aluminum in said alloy composition amounts to at least 20% by weight of said alloy composition, and the weight of zirconium therein amounts to not more than 75% by weight of said alloy composition; said alloy composition being free from copper, cobalt, nickel, vanadium and tin, apart from the usual impurities.

2. Implant according to claim 1, wherein said implant is a device for internal fixation.

3. Implant according to claim 2, wherein said device comprises a plate for securing bone fragments together.

4. Implant according to claim 3, wherein said plate has at least one opening therethrough for a securement device.

5. Implant according to claim 2, wherein said device comprises a screw.

6. Implant according to claim 2, wherein said device comprises a nail or pin.

7. Implant according to claim 6, wherein said device has at least one opening therethrough for a securement devive.

8. Method of using a durable, workable, non-toxic alloy as an implant for bone, joint or dental surgery which comprises providing an implant of a worked and heat-treated alloy composition consisting essentially of
   i. a first component constituting from about 3% to about 30% by weight of said alloy composition and consisting essentially of not less than one member selected from the group consisting of niobium, tantalum, chromium, molybdenum, and aluminum; and the balance
   ii. a second component consisting of not less than one member selected from the group consisting of titanium, and zirconium wherein the sum of the weights of chromium, molybdenum, and aluminum in said alloy composition amounts to not more than 20% by weight of said alloy composition, and the weight of zirconium in said alloy composition amounts to not more than 75% by weight of said alloy composition; said alloy composition being free from copper, cobalt, nickel, vanadium, and tin, apart from the usual impurities, said alloy composition having a tensile strength of at least about 100 kg/mm² and fatigue strength of at least about 40 kg/mm², and positioning said implant in a living subject undergoing bone joint or dental surgery for internal fixation or repair of a fractured bone, joint or tooth.

9. The method of claim 8, wherein up to about 1% by weight of said alloy composition is dissolved gas.

10. The method of claim 9, wherein said gas is a member selected from the group consisting of oxygen, nitrogen, hydrogen and a carbon containing gas.

11. The method of claim 8, wherein said first component contains about 3% by weight niobium and about 6% by weight aluminum based on said alloy, and said second component consists essentially of titanium.

12. The method of claim 8, wherein said first component contains from about 8% to about 9% by weight niobium, about 11% by weight chromium and about 3% by weight aluminum based on said alloy, and said second component consists essentially of titanium.

13. The method of claim 8, wherein said first component contains about 4% by weight molybdenum and about 48% by weight zirconium based on said alloy, and said second component consists essentially of titanium.

14. Method of making an implant for bone, joint or dental surgery, which comprises:
   a. providing a worked and heat-treated alloy composition having full tissue compatibility, said alloy composition consisting essentially of:
      i. a first component of said alloy composition constituting about 3% to about 30% by weight thereof, and consisting essentially of not less than one member selected from the group consisting of niobium, tantalum, chromium, molybdenum, and aluminum; and the balance
      ii. a second component of said alloy composition consisting essentially of not less than one member selected from the group consisting of titanium, and zirconium,
   wherein the sum of the weights of chromium, molybdenum and aluminum in said alloy composition about to not more than 20% by weight of said alloy, and the weight of zirconium therein amounts to at most 75% by weight of said alloy composition; said alloy composition being free from copper, cobalt, nickel, vanadium and tin, apart from the usual impurities;
   b. shaping the alloy composition to the desired form of implant; and
   c. subjecting the so-shaped alloy composition to heat treatment, whereby an implant is obtained composed of alloy having a tensile strength at least about 100 kg/mm$^2$ and fatigue strength of at least about 40 kg/mm$^2$.

15. The method as claimed in claim 14, wherein a dissolved gas, constituting at most 1% by weight of said alloy is added to the alloy.

16. The method as claimed in claim 14, wherein said first component consists essentially of 3% by weight of niobium and 6% by weight of aluminum, all based on said alloy and wherein said second component consists essentially of titanium.

17. The method of claimed in claim 14, wherein said first component consists essentially of from about 8% to about 9% by weight of niobium, about 11% by weight of chromium and about 3% by weight of aluminum, all based on said alloy, and wherein said second component consists essentially of titanium.

18. The method as claimed in claim 14, wherein said first component consists essentially of about 4% by weight of molybdenum and about 48% by weight of zirconium, based on said alloy, and wherein said second component consists essentially of titanium.

* * * * *